Figures 1, 2:
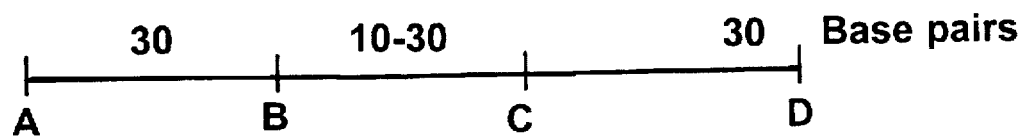

US005665538A

United States Patent [19]
Slater et al.

[11] Patent Number: 5,665,538
[45] Date of Patent: Sep. 9, 1997

[54] ULTRASENSITIVE MICROTRACE PROCEDURE FOR MONITORING THE ORIGIN OF A MATERIAL

[76] Inventors: James Howard Slater, 38 Heol-Y-Deyln, Lisvane, Cardiff CF4 5SR; John Edward Minton, 2 Mill Place, Lisvane, Cardiff CF4 5TF, both of Great Britain

[21] Appl. No.: 946,336
[22] PCT Filed: May 7, 1991
[86] PCT No.: PCT/GB91/00719
  § 371 Date: Dec. 29, 1992
  § 102(e) Date: Dec. 29, 1992
[87] PCT Pub. No.: WO91/17265
  PCT Pub. Date: Nov. 14, 1991

[30] Foreign Application Priority Data

May 4, 1990 [GB] United Kingdom ............. 9010138

[51] Int. Cl.$^6$ .................................................. C12Q 1/68
[52] U.S. Cl. ............... 435/6; 436/56; 436/27; 44/600; 44/628; 435/91.2
[58] Field of Search ............... 435/6, 91.2; 536/24.32, 536/25.33, 25.41; 436/56, 27; 44/600, 628

[56] References Cited

U.S. PATENT DOCUMENTS

| | | | |
|---|---|---|---|
| 3,861,886 | 1/1975 | Meloy | 44/51 |
| 4,441,943 | 4/1984 | Kydd | 149/109.4 |
| 4,511,713 | 4/1985 | Miller et al. | 536/27 |

FOREIGN PATENT DOCUMENTS 0 288 737 11/1988 European Pat. Off. ......... C12Q 1/68
WO87/06383 10/1987 WIPO ......... C12Q 1/68
WO90/14441 11/1990 WIPO ......... C12Q 1/68

OTHER PUBLICATIONS

Nagata et al. Quantification of Picogram Levels of Specific DNA Immobilized in Microfiter Wells, FEBS Letters (Apr. 1985) 183:379–382.

Matthews, J.A. et al. Review: Analytical Strategies for the Use of DNA Probes, Anal Biochem (1988) 169:1–25.

Thuong, N.T., et al. Synthese Et Reactivite D'Oligothymidylates Substitues Par Un Agent Intercalant Et Un Groype Thiophosphate, Tetrahedron Letters (1987) 28:4157–4160.

Zwadyk, P., Jr. et al. Commercial Detection Methods For Biotinylated Gene Probes Comparison With Phosphorous 32 Labeled DNA Probes, Curr Microbiol. (1986) 14: 95–100, Abstract.

International Search Report, PCT Application No. PCT/GB91/00719 (dated May 7, 1991).

P.S. Miller, et al, A New Approach To Chemotherapy Based On Molecular Biology And Nucleic Acid Chemistry: Matugen ... Anti-Cancer Drug Design (1987) 2:117–128.

Primary Examiner—W. Gary Jones
Assistant Examiner—Amy Atzel
Attorney, Agent, or Firm—Fish & Richardson, P.C.

[57] ABSTRACT

A method of monitoring the movement of a material which comprises adding to the material, as a microtrace additive, DNA molecules, sampling the resulting material after movement thereof and detecting the presence of said microtrace additive in the sample. The method is particularly suitable for use in monitoring the movement of oil shipments and the microtrace additive is selected such that it will remain in the oil phase in the event the oil is dispersed in water e.g. sea water.

10 Claims, 1 Drawing Sheet

| A | pa30 | B | 10-30 | C | ca30 | D |
|---|---|---|---|---|---|---|
| 18/20 \<base\> for PCR primers | 10 \<base\> for DNA sequencing primers | | | | methylated DNA with same structure as AB region | |
| aqueous phase | | | | | hydrocarbon phase | |

```
A      pa30        B      10-30      C      ca30         D
─────────────────────────────────────────────────────────────
18/20              10                    │ methylated DNA
<base>             <base>                │ with same
for PCR            for DNA               │ structure as
primers            sequencing            │ AB region
                   primers               │
                                         │
aqueous                                  │ hydrocarbon phase
phase                                    │
```

ULTRASENSITIVE MICROTRACE PROCEDURE FOR MONITORING THE ORIGIN OF A MATERIAL

The present invention relates to a method and procedure which enables any material (liquid or solid) to be traced from one location to another and in particular to a method of tracing the origin of petroleum products such as oils.

There is a widespread requirement to be able to trace the path taken by a given material as it moves from one location to another. In general terms two broad categories of material movement are encountered. Firstly, the movement of materials as a result of natural processes occurring in the biosphere. For example, the flow of water in sub-surface aquifers, or the movement and partitioning of water bodies as seen in ocean currents, or the movement of sediments. Secondly, the movement of materials which have been manufactured by man (i.e. items which do not occur in the natural environment) or which are natural materials being transported as a result of man's activities. The former would include any item produced by man, the latter would include items such as grain (or other food materials), mineral ores or petroleum products such as crude oil.

In all these situations, there may be reasons why it is necessary to develop specific procedures to trace these movements. It might be that direct observation is not practicable, for example, following the path taken by a stream flowing underground cannot be directly observed at all points in its passage. It might be that it is necessary to monitor the movement of goods without the direct knowledge of the transporters. It might be that for legal reasons it is necessary to prove that the appearance of a material at a particular point in the biosphere was due to the same material originating from a known starting point. Whatever the reason, be it of scientific or commercial interest, accurate, quantifiable, reliable and preferably unique tracing procedures are required.

One detailed requirement which illustrates the features generally described above may be the following. It is undesirable and in certain circumstances illegal, for petroleum materials to leak from storage sites or transportation containers and contaminate the natural environment. Usually petrol storage tanks (for example, at petrol filling stations) are located underground. Normally there is more than one tank at each site. Should one of these tanks develop a leak, eventually the loss of material will be detected either by audits on the material being added to and removed from the storage tank, or by detection of spilt, leakage material at some site adjacent to the storage tank area. Since the tanks are underground visual inspection is not possible and it is a costly procedure to excavate and determine which tank may be leaking. The normal procedure would be to develop a protocol whereby a known material, for example, a dye, is added to the tanks and by tracing the movement of the dye determine which tank is the cause of the leakage. Cheaper remedial action can then be taken to deal with the identified leaking tank. A feature of this procedure is that the materials added to each tank must be different in order to know which tank is leaking (i.e. if there are six tanks, six different dyes recognisable by some property which can be accurately and uniquely determined need to be used). The greater the number of individual components in a particular system the greater the number of unique traces need to be used to make the necessary distinction between the paths taken by different leaks from different tanks.

A further requirement concerns the identification of the source of pollution in the sea and waterways from spills of petroleum materials, particularly oil. The environmental damage caused by accidental oil spills and deliberate dumping of oil by ships, e.g. when washing tanks, is significant and there is a demand for the culprits to be identified and to be held responsible for clean-up operations. One of the problems associated with the identification of oil samples in large volumes of aqueous media e.g. an oil slick in the sea, is that any microtrace or identifier introduced into oil has a tendency to partition out or be dispersed in the aqueous phase rendering collection and identification of the microtrace particularly difficult.

Many tracing methods have been used to solve problems of this sort, all involving the addition of some characteristic material. Previously such additives have been dyes, or radioactive compounds, or characteristic organic molecules, or cellulose microdots. Biological materials have also been used, notably for tracing the movement of water bodies in the natural environment, such as bacteriophage or bacteria. In these cases the living systems possess some property (for example, a known drug resistance pattern, or particular host specificity) which does not normally occur in nature. The added organisms can be traced from their point of addition by measuring samples as required, isolating the added organisms and showing that organisms isolated from samples are the same as those originally added.

International Patent Publication No. WO 90/14441 published on 29th Nov., 1990 discloses a method of monitoring the presence of a substance which comprises tagging the substance with a nucleic acid, collecting the substance and detecting said nucleic acid, generally by amplifying the nucleic acid using polymerase chain reaction technology. Suitable substances which may be tagged are said to include air pollutants, oils, aromatic compounds, explosive compositions, foodstuffs, medicaments, inks, paper goods and paint products. It is stated the nucleic acids can be optionally bound to a component of the tagged substance through a covalent bond i.e. that the nucleic acids are covalently bound to the tagged material or a component thereof. Alternatively, the nucleic acids may be free or they may be bound to a solid support (such as latex beads, dextran or magnetic beads) which is then mixed with the material being tagged.

International Patent Publication No. WO 90/14441 discloses that oils and other non-polar liquids can be tagged effectively by the use of detergents added to the taggant prior to the addition of the taggant to the liquid. Recovery of taggant may be achieved by standard techniques. Typically, the sample is washed or extracted with either distilled water or a buffered solution. Using phenol based extractions or phenol/chloroform extractions one can recover nucleic acid from complex biological substances or from oil based substances.

International Patent Publication No. WO 90/14441 does not appreciate the problem of tagging petroleum products in a manner which will withstand prolonged mixing with vast amounts of aqueous phase nor disclose the possibility of tagging immense volumes of oil, e.g., thousands of tonnes, which are currently routinely carried over the seas by tankers. The specific example of tagging oil comprises:

Preparation: (a) mix together 40 µg of taggant, 10 µl "Tween 80" (detergent), 10 µl "Span 80" (detergent), and 100 µl distilled water, and (b) add mixture to 1.7 ml oil. The combination is then thoroughly mixed.

Recovery: add oil directly to PCR mix (which is an aqueous based mixture), vortex and amplify; or use a standard phenol-chloroform extraction. After treatment with phenol, the taggant was detected in the boundary layer between the oil and water phases. A brief description of the drawings follows: FIG. 1 is a diagram which represents a model microtrace DNA molecule of this invention. FIG. 2 is a diagram which represents the same DNA molecule shown in FIG. 1 with more details.

This invention describes the use of a particular biological material which can be used to monitor the movement of materials in any of the general ways envisaged above. The biological material used is a complex molecule whose structure can be characterised in several ways and in principle an infinite number of unique molecules can be generated to produce an infinite number of different, unique microtrace additives. In practise, the natural variability of the molecule can be manipulated to give a measurable value for the likelihood of such a similar molecule occurring naturally. That is, by careful selection of molecules for the microtrace material complete certainty within prescribed limits of probability can be calculated to show that there can be only one outcome of a particular trace pattern. The present intervention makes use of recent advances in highly sensitive methods for the detection of the presence of this biological molecule at exceedingly low levels or concentrations. Moreover this procedure, although based on a biological molecule, does not depend on the system being living within the normal definition of living, i.e., capable of sustained replication from one generation to the next.

The biological molecule to be used as the microtrace additive is DNA (deoxyribose nucleic acid), the genetic information molecule of almost all living systems. Each DNA molecule can be unique as a result of the sequence of bases (adenine, thymine, cytosine and guanine) contained within the molecule. Probability terms can be calculated for the frequency of a given sequence of bases and, so long as sufficient bases are used (i.e., a sufficiently big DNA molecule is employed as the microtrace additive) then for all practical purposes a unique microtrace can be defined and used. Previously DNA (or other biological molecules) could have been used as trace molecules, but the sensitivity of all known analytical procedures precluded their use since large quantities of DNA would have been needed. Addition of such quantities as a trace may have been undesirable and moreover the process would have been uneconomic.

This invention described the use of small quantities of DNA (typically in the concentration range 1000 to 0.01 pg DNA/µl) because of the technical ability to determine the presence of DNA molecules made possible by the polymerase chain reaction method. In vitro methods have been described which allow for the enzymatic amplification of specific DNA sequences using oligonucleotide primers which recognise all or part of the DNA molecule used as the microtrace additive. The sequential use of the polymerase chain reaction enables the molecule to be amplified exponentially. For example, 25 complete cycles of amplification enable a single molecule to be increased $3.4 \times 10^7$ times.

For example 2000 pg of plasmid pBR322 DNA was added to 100 µl of Arabian light crude oil and mixed. This represented the addition of a microtrace molecule to a sample. Any concentration of Plasmid pBR322 DNA could have been used which gave a final concentration in the range 1000 to 0.01 pg DNA/µl. For this example pBR322 DNA was also chosen because known DNA primers for DNA amplification were available. To extract the DNA 100 µl distilled water was added and the hydrocarbon/water mixture thoroughly mixed by mechanical agitation to extract the pBR322 DNA from the hydrocarbon into the aqueous phase. The complete mixture was centrifuged at 10,000× g for 5 minutes and 5 µl of the aqueous phase layer removed and loaded into a standard Taq Polymerase PCR reaction vial and reaction mixture (100 µl containing 50 mM KCl, 10 mM Tris HCl (pH 8.4) buffer; 1.5 mM MCl$_2$, 100 µg/ml gelatin, 0.25 µm of two pBR322 DNA primers; 200 µm of each deoxyribose nucleotide phosphate (dATP, dCTP, dGTP, dTTP and 2.5 units of Taq polymerase). Following automated PCR cycling, 10 µl of reaction mixture was loaded onto 2% (w/v) agarose gel and electrophoresed under standard conditions. The completed gel was stained with ethidium bromide to visualise the amplified DNA. No bands appeared in various negative controls. This procedure showed that DNA could be detected in oil samples following use as a microtrace indicator. The procedure also illustrates that the plasmid will partition into the aqueous phase and would not be suitable as a trace additive for oil which is likely to be spilt in the sea etc., because the microtrace would be washed out of the oil rendering the labelling useless.

Any material could be traced: it might be petroleum products; manufactured goods; water bodies; oil spillages, etc, provided that an appropriate DNA microtrace molecule had been added. Preferably the DNA molecule added will be a known sequence with known DNA primers in order to initiate the DNA polymerase amplification. However, this need not be the case: any DNA could be used and visualised using the following procedure.

DNA can be isolated from a sample following its addition as a microtrace compound, and cleaved into small fragments using any suitable restriction endonuclease (e.g. EscoRI, PstI, HindIII, etc). To the digested or partially digested DNA, known sequence double stranded linker molecules (typically of 15 to 25 bp long) can be added and ligated to the digested DNA molecules using DNA ligase enzymes. DNA amplification of the DNA sample molecule could then be achieved using single stranded DNA primers which recognise the DNA linkers bonded to the microtrace DNA.

The uniqueness of the microtrace DNA molecule can be pre-determined using specific DNA base sequences. The DNA microtrace molecules may be ones which occur naturally, such as pBR322, and for which a known sequence has been determined (by DNA sequencing procedures). The DNA used may be synthesised DNA using a pre-determined sequence of bases DNA primers and linkers for unique recognition which can be routinely synthesised. The uniqueness of the microtrace DNA, primers and linkers is known only to the individual who adds the microtrace molecule, thereby guaranteeing security of microtrace paths.

The DNA may be added directly as a naked molecule or as part of a complete organism (phage, bacteria, fungus or protozoa). The DNA may be formulated into materials which protect the DNA whilst it is present in the material being traced (e.g. as a bead surrounded by a gelatin coat, or surrounded by another protective polymer). DNA may be formulated in such a way as to ensure that it dissolves or bonds to the material being traced (e.g. for use in hydrocarbons it may be formulated within a hydrocarbon soluble material which ensures the DNA dissolves in the hydrocarbon and cannot be removed easily by aqueous washing). Also, DNA can be covalently linked to hydrophobic beads which are lipophilic and form stable dispersions in liquid hydrocarbons.

For example, the DNA may be formulated as follows to ensure the DNA remains within the hydrocarbon and cannot be removed from the hydrocarbon by aqueous washing. In mixtures of water and hydrocarbons, for example, oil spills at sea, any DNA present in the hydrocarbon tend to move to the aqueous phase. The partitioning of DNA under these conditions is due to the negative charges associated with the phosphodiester groups of the DNA and the ability to form hydrogen bonds with water molecules and an inability to do so in a hydrocarbon environment. The negative charges associated with the phosphodiester structures of the DNA molecule can be removed by methylation of these groups. Methylation of a region of the DNA molecule will ensure that this part of the molecule becomes hydrophobic thereby ensuring that the DNA molecule remains within the hydrocarbon phase and is not transferred to the aqueous phase. This can be achieved even if part of the DNA molecule retains its negative charge, i.e., is non-methylated. Methylation of the DNA molecule can be achieved by synthesising the DNA oligonucleotides used as the microtrace molecules with nucleosides which are in turn synthesised with methyl phosphonates.

Any procedure which favours solubilisation of DNA molecules in hydrocarbons instead of an aqueous phase could be used as an alternative to methylated DNA. This could be accomplished by labelling DNA on the nucleoside bases with biotin, or hydrophobic haptens such as fluorescein, dinitrophenol or tri-iodothyronine. Biotinylated DNA tends to partition into non-aqueous phases, such as hydrocarbons. Alternatively sulphonucleotides containing thiophosphates could be used and incorporated into the microtrace DNA and subsequently derivatised with thiol-specific modifying agents such as iodoethanol.

Whatever procedure is used to modify the microtrace DNA to anchor it into the hydrocarbon phase, for the purposes of the applications stated here, it will be necessary to remove the microtrace DNA into an aqueous phase in order to amplify the DNA using polymerase chain reaction procedures and for subsequent label determination. This can be accomplished directly or indirectly as follows. The anchored microtrace DNA will have attached, at the opposite end to the methylated sequence of DNA, a biotin molecule. The microtrace DNA labelled hydrocarbon (or other non-polar material) will then be mixed with particles coated with streptavidin. Biotin-streptavidin has a very high binding constant (almost irreversible) thereby ensuring that the DNA attached to the biotin will be extracted from the hydrocarbon. The particles now containing streptavidin-biotin-DNA can be removed by any suitable separation technique and used directly in PCR reaction mixtures.

Alternatively, the streptavidin can be coated on a solid surface and the oil containing the biotin-DNA washed over the surface. Excess hydrocarbon can then be washed off by an appropriate solvent leaving the biotin-DNA bound to the surface via the streptavidin molecule.

An outline system is as follows:

1. The microtrace DNA could be a synthetic DNA sequence of 70–90 base pairs as shown in FIG. 1.
2. The regions AB and CD will be constant for all microtrace DNA molecules and will carry predetermined sequences which recognise appropriate complementary primers for use:
   a. in PCR amplification and,
   b. in DNA sequencing of PCR amplified DNA.
3. The region BC is the variable region of the microtrace DNA and it will be this region which gives each microtrace DNA molecule its unique, characteristic signal. If this region is 10 bases long then with the four bases available for a DNA molecule, there will be $1.048 \times 10^6$ unique microtrace molecules capable of being synthesised. If the BC region is 15 bases long, then $1.07-10^9$ unique microtrace molecules can be synthesised. If the BC region is 30 bases, then $1.15 \times 10^{18}$ unique microtrace molecules can be synthesised.
4. The region CD will be synthesised with methylated nucleosides to provide the hydrocarbon anchoring properties.
5. The biotin molecule for extracting by streptavidin binding will be attached to point A.
6. Thus, the model microtrace DNA may look like the diagram shown in FIG. 2:

AB and CD regions will be identical and constant for all microtrace molecules, except that the CD is methylated, AB is non-methylated and the biotin molecule is bound to point A.

In the case of DNA labelled with hydrophobic haptens, separation from a sample may be achieved by making use of hapten/antibody pairings in a similar manner to biotin/streptaridin as discussed above.

In an alternative way to ensure that the DNA remains within the hydrocarbon, the microtrace DNA may be covalently linked to hydrophobic beads designed to be soluble in hydrocarbons and not in the aqueous phase. Such beads generally have a size in the range 1 to 5 microns. If only a few oligonucleotides, but enough for subsequent PCR amplification, sequence analysis and decoding, were added and bonded to the beads, the proportion of hydrophilic surface (due to the DNA oligonucleotides) compared with the overall hydrophobic surface (due to the composition of the bead) would be insufficient to cause the DNA-bead complex to partition into the aqueous phase. It would remain in the hydrocarbon until some procedure was used to remove the bead plus its attached oligonucleotide from the hydrocarbon.

DNA can be attached to the chosen hydrophobic beads in a number of ways. Beads such as paramagnetic carboxyl modified polystyrene beads (Polysciences, Northampton UK) or paramagnetic tosyl-activated polystyrene beads (Dynal, Merseyside UK) may be used in this context. The DNA oligonucleotide can be attached covalently by linking the 5' terminal free amino acid to a suitable target, in this case a carboxyl group attached to the bead. The method is routine (Lund et al., Nucleic Acid Research 16, 10861, 1980). Following oligonucleotide attachment, the labelled beads can be washed in water and air dried. The excess carboxyl groups on the beads which have not been bonded to an oligonucleotide, can be capped with octylamine dissolved in an aqueous solvent such as DMF using DCC as the cross-linking reagent.

Oligonucleotide labelled beads can be dispersed in solvents such as chloroform, ether, petroleum ether or toluene which in turn can be dispersed in the oil to be labelled ensuring an even distribution of the beads and hence the DNA in the oil. The beads can be separated for DNA determination and evaluation of the label by using magnets to pull the beads into one region from which they can be physically separated, or simply by centrifugation. Care must be taken to ensure that the beads have a specific gravity which is the same as the oil in order to prevent sedimentation and so an uneven distribution of the label.

The microtrace additive must be thoroughly dispersed into the material. In the case of oil, the microtrace additive may conveniently be incorporated into the oil when the oil is pumped into a storage container or vessel by means of dosing pumps known in the art.

We claim:

1. A method of monitoring the movement of a petroleum material in an aqueous medium comprising, adding a microtrace additive to the petroleum material, wherein the microtrace additive is DNA in a final concentration in the range of 0.01 to 1000 pg/DNA/µl petroleum material, and wherein the DNA is formulated to be soluble in said petroleum material such that the overall hydrophobicity of the microtrace additive causes it to partition into the petroleum material, and wherein said formulation ensures that the DNA is dissolved in or dispersed within the petroleum material such that it essentially cannot be removed by aqueous washing;

sampling the microtrace additive-containing petroleum material after movement thereof;

removing the microtrace additive from the petroleum material; and detecting the DNA microtrace additive by means of an amplification reaction.

2. The method according to claim 1, wherein the microtrace additive dissolves in the petroleum material.

3. The method according to claim 1, wherein the petroleum material is oil.

4. The method according to claim 1, wherein DNA is linked to a hydrophobic hapten to produce said microtrace additive and wherein said microtrace additive is removed from the sample by contacting the sample with a solid phase coated with an antibody for the hapten, wherein the hydrophobic hapten is selected from the group consisting of fluorescein, dinitrophenol, ahd triiododthyronine.

5. The method according to any one of claims 1, 2, or 3, wherein the microtrace additive is DNA comprising sulfonucleotides that contain thiophosphates modified by suitable agents to render the DNA molecule hydrophobic.

6. A composition consisting essentially of a microtrace additive dissolved in or dispersed in a petroleum material, wherein said microtrace additive is DNA in a final concentration in the range of 0.01 to 1000 pg/DNA/µl petroleum material, and wherein the DNA is formulated to be soluble in said petroleum material such that the overall hydrophobicity of the microtrace additive causes it to partition into the petroleum material, and wherein said formulation ensures that the DNA is dissolved in or dispersed within the petroleum material such that it essentially cannot be removed by aqueous washing.

7. The composition of claim 6, wherein said microtrace additive is dispersed in said petroleum material.

8. The composition of claim 6, wherein said microtrace additive is dissolved in said petroleum material.

9. The composition of claim 6, wherein the DNA is linked to a hydrophobic bead.

10. The composition of claim 7, wherein said petroleum material is oil.

* * * * *